(12) United States Patent
Bailey et al.

(10) Patent No.: US 10,610,313 B2
(45) Date of Patent: Apr. 7, 2020

(54) SURGICAL INSTRUMENT WITH SHIFTABLE TRANSMISSION

(71) Applicant: INTUITIVE SURGICAL OPERATIONS, INC., Sunnyvale, CA (US)

(72) Inventors: David W. Bailey, Portola Valley, CA (US); Theodore W. Rogers, Alameda, CA (US); Rumen Deyanov, Fremont, CA (US); Ray Lathrop, Nashville, TN (US); Gabriel Brisson, Albany, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 773 days.

(21) Appl. No.: 15/129,252

(22) PCT Filed: Mar. 31, 2015

(86) PCT No.: PCT/US2015/023636
§ 371 (c)(1),
(2) Date: Sep. 26, 2016

(87) PCT Pub. No.: WO2015/153642
PCT Pub. Date: Oct. 8, 2015

(65) Prior Publication Data
US 2017/0172672 A1    Jun. 22, 2017

Related U.S. Application Data

(60) Provisional application No. 61/973,257, filed on Mar. 31, 2014.

(51) Int. Cl.
*A61B 34/30* (2016.01)
*A61B 34/37* (2016.01)
(Continued)

(52) U.S. Cl.
CPC .............. *A61B 34/30* (2016.02); *A61B 17/29* (2013.01); *A61B 34/37* (2016.02); *A61B 34/70* (2016.02);
(Continued)

(58) Field of Classification Search
CPC ........ A61B 2017/00398; A61B 17/068; A61B 2017/00477; A61B 2017/00115; A61B 2017/00734
See application file for complete search history.

(56) References Cited

U.S. PATENT DOCUMENTS

| 5,184,601 A | 2/1993 | Putman |
| 5,445,166 A | 8/1995 | Taylor |

(Continued)

FOREIGN PATENT DOCUMENTS

| CN | 1864938 A | 11/2006 |
| EP | 1973021 A2 | 9/2006 |

(Continued)

OTHER PUBLICATIONS

Extended European Search Report for Application No. EP15772379.2, dated Oct. 26, 2017, 11 pages.

(Continued)

*Primary Examiner* — Shawki S Ismail
*Assistant Examiner* — Zoheb S Imtiaz
(74) *Attorney, Agent, or Firm* — Haynes and Boone, LLP

(57) ABSTRACT

A surgical tool having an elongated shaft having a proximal end and distal end. A surgical end effector is located about the distal end. The surgical end effector has a plurality of effector mechanisms comprising a plurality of degree of freedoms. An effector body is located at the proximal end. The effector body includes a plurality of motor interfaces for driving the plurality of effector mechanisms. A transmission is coupled to the effector body.

26 Claims, 13 Drawing Sheets

(51) Int. Cl.
  *B25J 9/16* (2006.01)
  *A61B 34/00* (2016.01)
  *A61B 17/29* (2006.01)
  *A61B 17/00* (2006.01)
(52) U.S. Cl.
  CPC ... *B25J 9/1669* (2013.01); *A61B 2017/00477* (2013.01); *A61B 2034/305* (2016.02)

(56) References Cited

U.S. PATENT DOCUMENTS

| | | |
|---|---|---|
| 5,797,900 A | 8/1998 | Madhani et al. |
| 5,800,423 A | 9/1998 | Jensen |
| 5,807,378 A | 9/1998 | Jensen et al. |
| 5,808,665 A | 9/1998 | Green |
| 5,855,583 A | 1/1999 | Wang et al. |
| 6,246,200 B1 | 6/2001 | Blumenkranz et al. |
| 6,676,669 B2 | 1/2004 | Charles et al. |
| 6,702,805 B1 | 3/2004 | Stuart |
| 6,758,843 B2 | 7/2004 | Jensen |
| 6,788,018 B1 | 9/2004 | Blumenkranz |
| 7,594,912 B2 | 9/2009 | Cooper et al. |
| 7,763,015 B2 | 7/2010 | Cooper et al. |
| 7,963,913 B2 | 6/2011 | Devengenzo et al. |
| 8,616,431 B2 | 12/2013 | Timm et al. |
| 8,640,788 B2 | 2/2014 | Dachs, II et al. |
| 8,852,174 B2 | 10/2014 | Burbank |
| 8,876,857 B2 | 11/2014 | Burbank |
| 2008/0058776 A1 | 3/2008 | Jo et al. |
| 2008/0272172 A1 | 11/2008 | Zemlok et al. |
| 2009/0101692 A1 | 4/2009 | Whitman et al. |
| 2011/0118707 A1 | 5/2011 | Burbank |
| 2011/0118709 A1 | 5/2011 | Burbank |
| 2011/0118754 A1 | 5/2011 | Dachs, II et al. |
| 2011/0118778 A1 | 5/2011 | Burbank |
| 2011/0245844 A1* | 10/2011 | Jinno ............... A61B 34/71 606/130 |
| 2011/0290856 A1 | 12/2011 | Shelton, IV et al. |
| 2012/0199632 A1 | 8/2012 | Spivey et al. |
| 2012/0205419 A1 | 8/2012 | Weir et al. |
| 2012/0209314 A1 | 8/2012 | Weir et al. |
| 2012/0310254 A1 | 12/2012 | Manzo et al. |
| 2013/0105552 A1 | 5/2013 | Weir et al. |
| 2013/0282023 A1 | 10/2013 | Burbank et al. |
| 2013/0325034 A1 | 12/2013 | Schena et al. |
| 2014/0001234 A1 | 1/2014 | Shelton, IV et al. |
| 2014/0200596 A1 | 7/2014 | Weir et al. |
| 2014/0305994 A1* | 10/2014 | Parihar ............ A61B 17/068 227/180.1 |
| 2017/0172672 A1 | 6/2017 | Bailey et al. |
| 2017/0281162 A1* | 10/2017 | Shelton, IV ....... A61B 17/0686 |

FOREIGN PATENT DOCUMENTS

| | | |
|---|---|---|
| EP | 1724071 A1 | 11/2006 |
| WO | WO-2006124390 A2 | 11/2006 |
| WO | WO-2011060318 A1 | 5/2011 |
| WO | WO-2011161626 A2 | 12/2011 |
| WO | WO-2013162217 A1 | 10/2013 |
| WO | WO-2015153642 A1 | 10/2015 |

OTHER PUBLICATIONS

Metal and Polymer Products to Help You Ligate with Security and Confidence, WECK Litigation Solutions, URL: https://www.teleflexsurgicalcatalog.com/brochures/2011-0039-S;;rLig_WeckLigation_Catalog.pdf, 2013, pp. 1-22.

International Search Report and Written Opinion for Application No. PCT/US15/23636, dated Jun. 10, 2015, 12 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

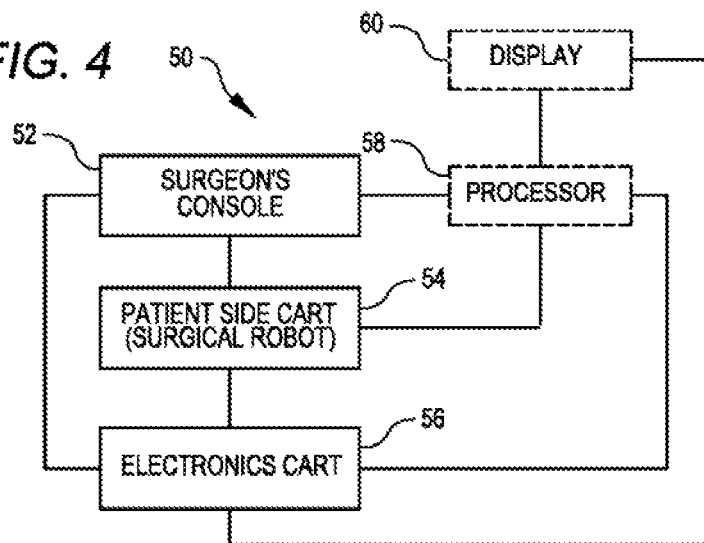
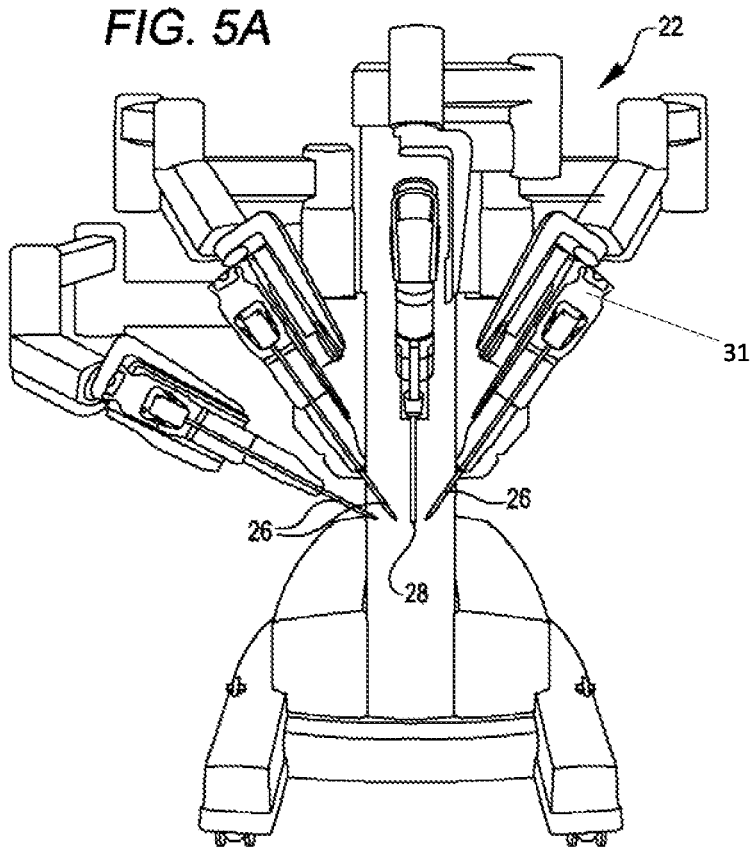

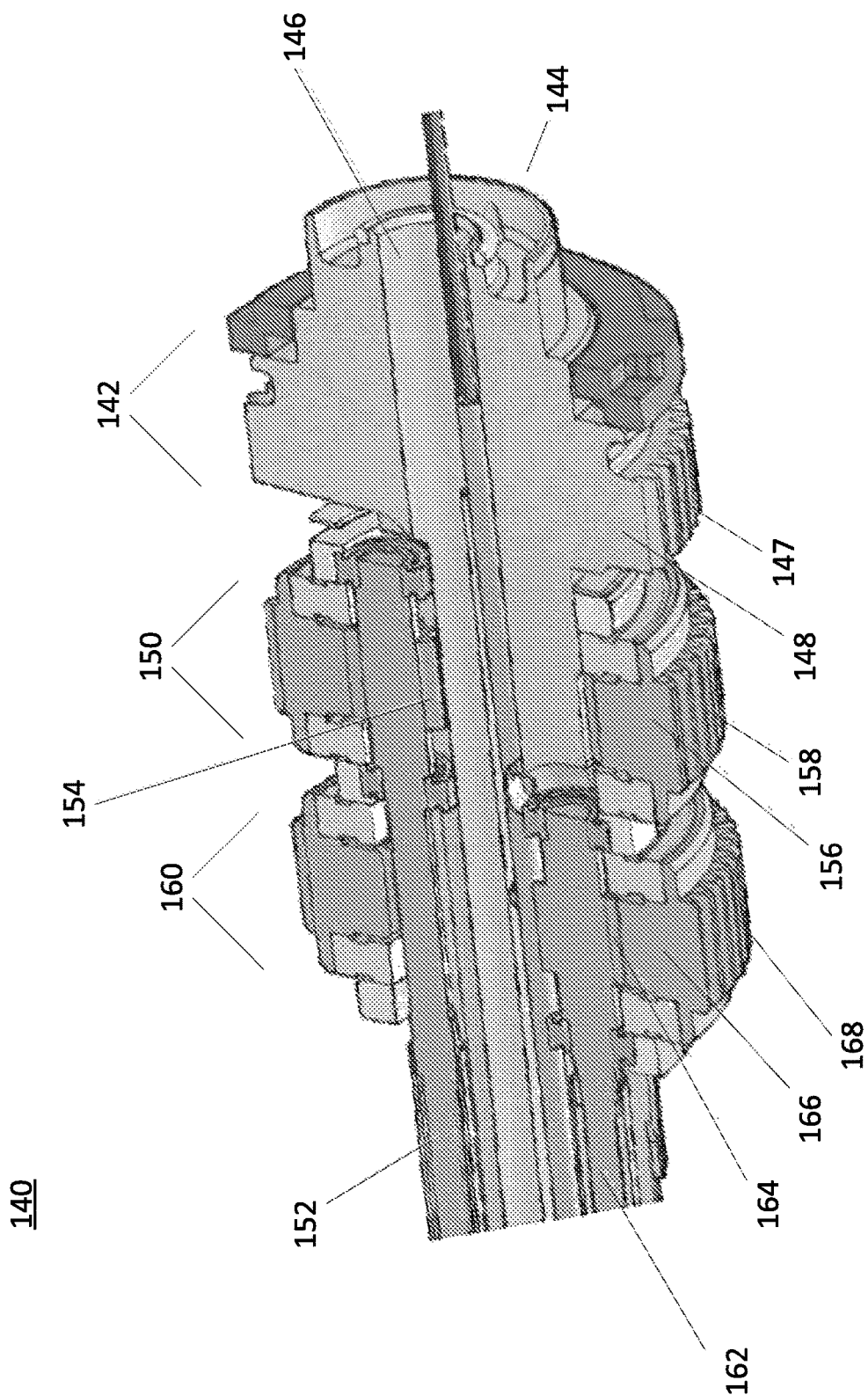

SURGICAL INSTRUMENT WITH SHIFTABLE TRANSMISSION

CROSS-REFERENCES TO RELATED APPLICATIONS

This application is the U.S. national phase of International Application No. PCT/US15/23636, filed Mar. 31, 2015, which designated the U.S. and claims the benefit of U.S. Provisional Application No. 61/973,257, filed Mar. 31, 2014, all of which are incorporated by reference herein, in their entirety.

BACKGROUND OF THE INVENTION

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive telesurgical systems have been developed to increase a surgeon's dexterity and avoid some of the limitations on traditional minimally invasive techniques. In telesurgery, the surgeon uses some form of remote control (e.g., a servomechanism or the like) to manipulate surgical instrument movements, rather than directly holding and moving the instruments by hand. In telesurgery systems, the surgeon can be provided with an image of the surgical site at a surgical workstation. While viewing a two or three dimensional image of the surgical site on a display, the surgeon performs the surgical procedures on the patient by manipulating master control devices, which in turn control motion of the servo-mechanically operated instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI® system available from Intuitive Surgical, Inc. of Sunnyvale, Calif., USA.

A variety of structural arrangements can be used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912; 6,758,843; 6,246,200; and 5,800,423; which are incorporated herein by reference. These linkages often make use of a parallelogram arrangement to hold an instrument having a shaft. Such a manipulator structure can constrain movement of the instrument so that the instrument pivots about a remote center of manipulation positioned in space along the length of the rigid shaft. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 7,763,015; 6,702,805; 6,676,669; 5,855,583; 5,808,665; 5,445,166; and 5,184,601; which are incorporated herein by reference.

A variety of structural arrangements can also be used to support and position the robotic surgical manipulator and the surgical instrument at the surgical site during robotic surgery. Supporting linkage mechanisms, sometimes referred to as set-up joints, or set-up joint arms, are often used to position and align each manipulator with the respective incision point in a patient's body. The supporting linkage mechanism facilitates the alignment of a surgical manipulator with a desired surgical incision point and targeted anatomy. Exemplary supporting linkage mechanisms are described in U.S. Pat. Nos. 6,246,200 and 6,788,018, which are incorporated herein by reference.

While the new telesurgical systems and devices have proven highly effective and advantageous, still further improvements are desirable. In general, improved minimally invasive robotic surgery systems are desirable. Often, new surgical instruments are developed for use on existing telesurgical system platforms. Thus, the instrument is required to adapt to the telesurgical system, since development of a new telesurgical system for a particular surgical application is cost prohibitive. However, issues arise when existing telesurgical platforms do not have the required amount of motor outputs for all of the mechanisms of a particular surgical instrument. Thus, there is a need to adapt new surgical devices to existing telesurgical systems without limiting the surgical capabilities and without requiring modification to the existing telesurgical systems.

BRIEF SUMMARY OF THE INVENTION

Many embodiments are directed to a surgical tool comprising an elongated shaft having a proximal end and distal end. A surgical end effector is located about the distal end. The surgical end effector may include a plurality of effector mechanisms, each effector mechanism having one or a plurality of degree of freedoms (DOFs). An effector body may also be located at the proximal end. The effector body may include a plurality of motor interfaces for driving the plurality of effector mechanisms. For example, the plurality of motor interfaces may include a first motor interface. A transmission may be coupled between the effector body and the surgical end effector. The transmission may be configured to shift coupling of the first motor interface between only a portion of the plurality of effector mechanisms and associated DOFs.

Many embodiments are directed to a surgical tool comprising an elongated shaft having a proximal end and distal end. A surgical end effector is located at the distal end of the shaft. The surgical end effector has a plurality of end effector components each associated with a unique mechanical degree of freedom. The plurality of end effector components has a first end effector component and a second end effector component. A drive mechanism is located at the proximal end of the shaft. The drive mechanism has a first motor interface and a transmission. The transmission includes a shift mechanism movable between a first state and a second state. In the first state the first motor interface is coupled via the transmission to drive the first end effector component without driving the second end effector component. In the second state the first motor interface being coupled via the transmission to drive the second end effector component without driving the first end effector component.

In many embodiments, the plurality of motor interfaces includes a second motor interface coupled to shift the shift mechanism between the first state and the second state.

In many embodiments, the plurality of end effector components includes a third end effector component. The shift mechanism may be movable to a third state. In the first state and in the second state the first motor interface is not driving the third end effector component. In the third state the first motor interface is coupled via the transmission to drive the third end effector component without driving the first and second end effector components.

In many embodiments, the plurality of motor interfaces includes a second motor interface coupled to shift the shift mechanism between the first state, the second state, and the third state.

In many embodiments, the first end effector component may be associated with a first end effector mechanical degree of freedom, and the second end effector component is associated with a second end effector mechanical degree of freedom. The drive mechanism may include a second motor interface coupled to drive a third end effector mechanical degree of freedom, a third motor interface coupled to drive a fourth end effector mechanical degree of freedom, and a fourth motor interface coupled to drive a fifth end effector mechanical degree of freedom. The first, second, third, fourth, and fifth mechanical degrees of freedom of the end effector are each unique.

In many embodiments, the plurality of end effector components includes a third end effector component associated with a sixth end effector mechanical degree of freedom. The first, second, third, fourth, fifth, and sixth mechanical degrees of freedom of the end effector are each unique.

In many embodiments, the plurality of motor interfaces includes a fifth motor interface coupled to shift the shift mechanism between the first state and the second state.

In many embodiments, the shift mechanism may include a rotatable camshaft, where a first position of the camshaft corresponding to the first state, and a second position of the camshaft corresponding to the second state.

In many embodiments, the plurality of motor interfaces further includes a second motor interface coupled to drive the camshaft.

In many embodiments, the transmission may include a rotatable camshaft. The camshaft can include a first camshaft position for shifting coupling of the first motor interface to a first DOF of the plurality of DOFs; a second camshaft position for shifting coupling of the first motor interface to a second DOF of the plurality of DOFs; and a third camshaft position for shifting coupling of the first motor interface to a third DOF of the plurality of DOFs.

In many embodiments, the plurality of motor interfaces further includes a second, third, fourth, and fifth motor interface, wherein the camshaft is driven by the second motor interface.

In many embodiments, the plurality of DOFs further includes a fourth DOF coupled exclusively with the third motor interface; a fifth DOF coupled exclusively with the fourth motor interface; and a sixth DOF coupled exclusively with the fifth motor interface.

In many embodiment, the surgical end effector can include a gripping device having a surgical tool, wherein the surgical end effector includes a wrist, the wrist being able to pitch, yaw, and roll the gripping device with respect to the remotely controlled arm.

In many embodiments, the first DOF is a mechanism for rolling the wrist; the second DOF is a mechanism for actuating the surgical tool; the third DOF is a mechanism for actuating the gripping device with high force relative to the sixth DOF; the fourth DOF is a mechanism for causing the wrist to yaw; the fifth DOF is a mechanism for causing the wrist to pitch; and the sixth DOF is a mechanism for actuating the gripping device with low force relative to the third DOF.

In many embodiments, the camshaft includes a plurality of camshaft lobes.

In many embodiments, the plurality of camshaft lobes includes a pair of lobes for powering and locking each of the first, second, and third DOFs.

In many embodiments, the transmission includes a first gear train for driving the first DOF, a second gear train for driving the second DOF, and a third gear train for driving the third DOF.

In many embodiments, the first gear train includes a first input gear; a first output gear ultimately coupled with the first input gear; a first rocker arm moveably engaged with the camshaft for engaging and disengaging the first input gear with the first output gear; a first locker arm moveably engaged with the camshaft for locking and unlocking the first output gear.

In many embodiments, the second gear train includes a second input gear; a second output gear ultimately coupled with the second input gear; a second rocker arm moveably engaged with the camshaft for engaging and disengaging the second input gear with the second output gear; and a second locker arm moveably engaged with the camshaft for locking and unlocking the second output gear.

In many embodiments, the third gear train includes a third input gear; a third output gear ultimately coupled with the third input gear; a third rocker arm moveably engaged with the camshaft for engaging and disengaging the third input gear with the third output gear; a third locker arm moveably engaged with the camshaft for locking and unlocking the third output gear.

In many embodiments, the first output gear may be coupled to a main shaft extending along and rotatable about an axis, and wherein the second and third output gears are held within the main shaft and rotate with the main shaft about the axis.

In many embodiments, the second output gear may be coupled to an first output shaft that extends within the main shaft, and the third output gear may be coupled to an second output shaft that extends within the main shaft.

In many embodiments, the first, second, and third gear trains may be arranged along a common axis that is parallel with the camshaft.

Many embodiments are directed to a method for shifting a transmission of a remotely controlled surgical apparatus. In the method, a transmission of a surgical device is shifted to engage one of a plurality of shiftable effector outputs to a surgical end effector of the surgical device. The surgical device may include a plurality of non-shiftable outputs. The surgical device may be connected to a remote controlled arm. The remote controlled arm may have a plurality of motors including a first motor for driving the transmission and a plurality of dedicated motors for driving the plurality of non-shiftable outputs. The one engaged shiftable effector output can be driven with the first motor to drive a corresponding effector mechanism of the surgical end effector.

Many embodiments are directed to a method in a surgical device comprising at least one of a first motor interface, a transmission, and an end effector comprising a first and a second component. The method includes operating the transmission in a first state, shifting the transmission from the first state to a second state, operating the transmission in the second state. and shifting the transmission from the second state to the first state. In the first state, the transmission couples the first motor interface to the first component of the end effector and decouples the first motor interface from the second component of the end effector. In the second state, the transmission couples the first motor interface with the second component of the end effector and decouples the first motor interface from the first component of the end effector.

In many embodiments, at least one of the plurality of non-shiftable effector outputs of the surgical end effector may be driven using a dedicated motor.

In many embodiments, shifting the transmission is caused by driving a camshaft of the transmission using a second motor.

In many embodiments, driving the camshaft is caused by rotating the camshaft to sequentially engage one of a plurality of gear trains.

In many embodiments, the camshaft is rotated to move a plurality of rocker arms that engage a plurality of gear trains of the transmission.

In many embodiments, rotating the camshaft causes at least one of the non-engaged gear trains to become locked.

In many embodiments, shifting can only occur sequentially along the plurality of gear trains.

In many embodiments, the plurality of effector shiftable outputs includes a first shiftable output for actuating the roll DOF, and high force grip DOF, and a tool actuation DOF.

In many embodiments, the wherein the plurality of dedicated DOFs comprises a yaw DOF, pitch DOF, and a low force grip DOF.

BRIEF DESCRIPTION OF THE DRAWINGS

FIG. 4 diagrammatically illustrates a telesurgically controlled surgery system, in accordance with many embodiments.

FIG. 5A is a partial view of a patient side cart of a telesurgically controlled surgery system, in accordance with many embodiments.

FIGS. 7A-7H are longitudinal and axial cross-sections of a transmission assembly of a telesurgically operated surgery tool, in accordance with many embodiments.

DETAILED DESCRIPTION OF THE INVENTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

I. Minimally Invasive Teleassisted Surgery System

Figure 1:
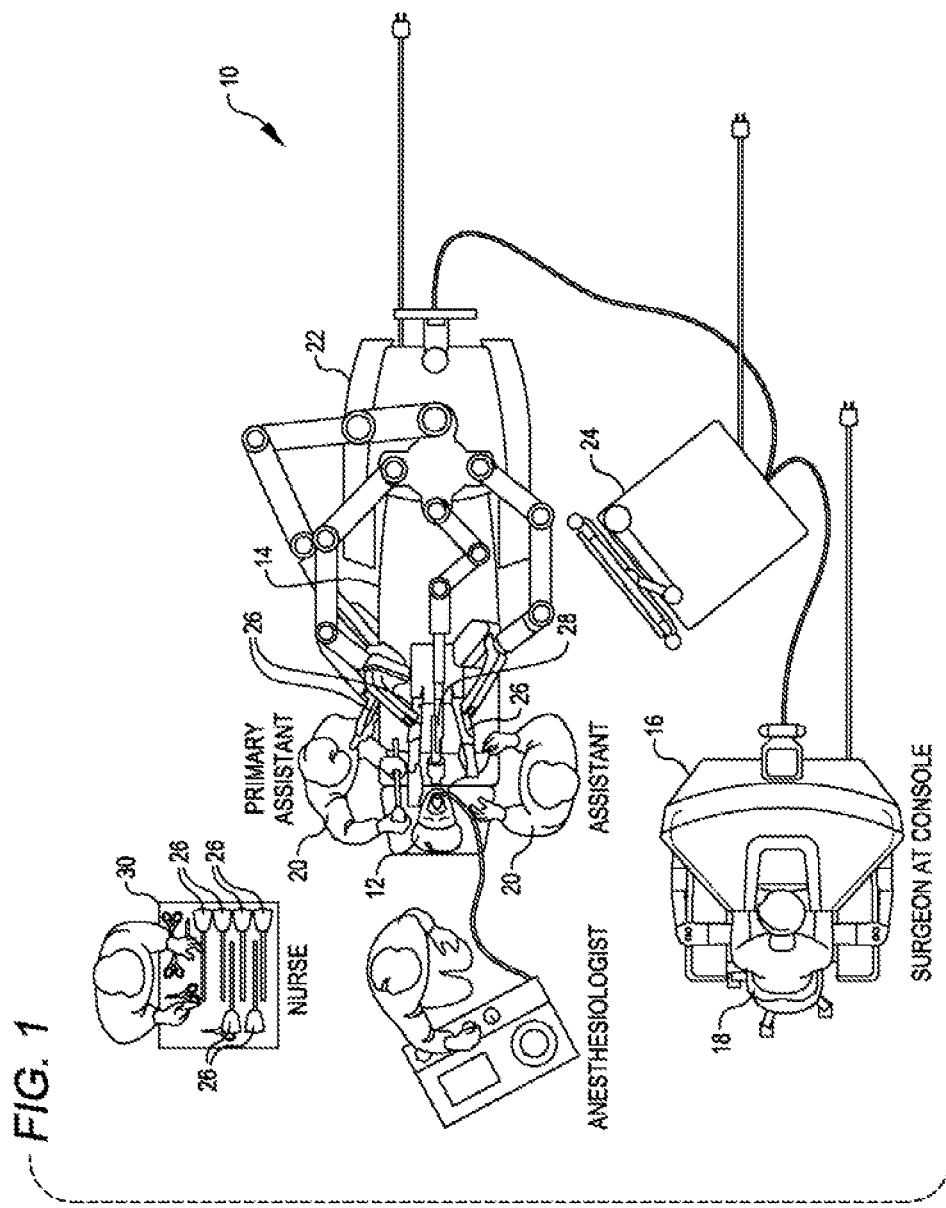
FIG. 1 is a plan view of a minimally invasive telesurgically controlled surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
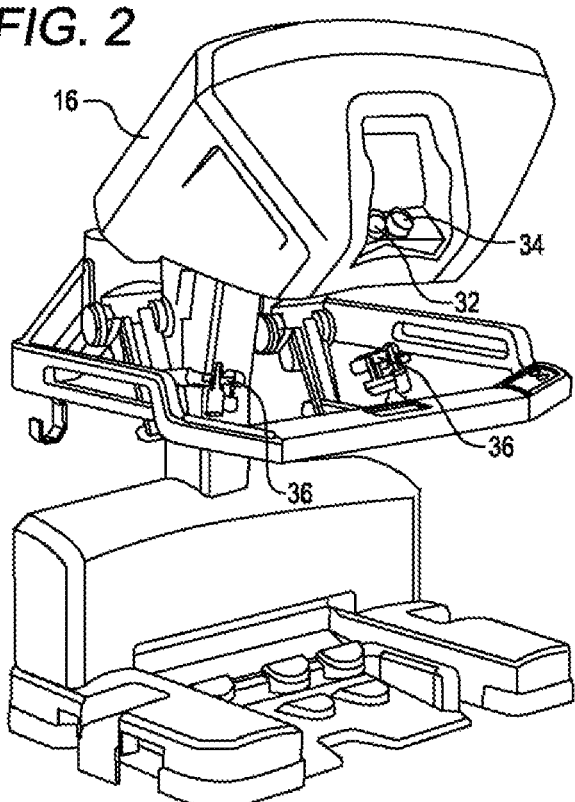
FIG. 2 is a perspective view of a surgeon's control console for a telesurgically controlled surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
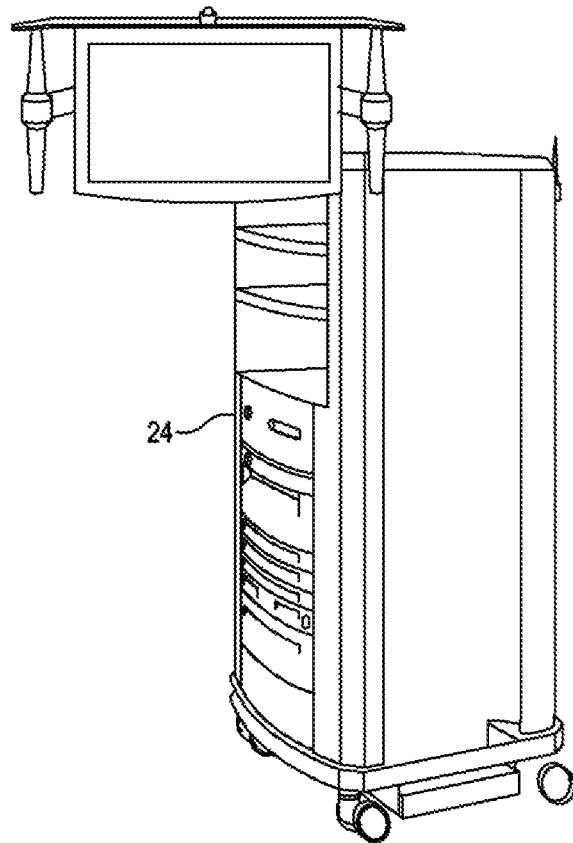
FIG. 3 is a perspective view of a telesurgically controlled surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patient Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5B:
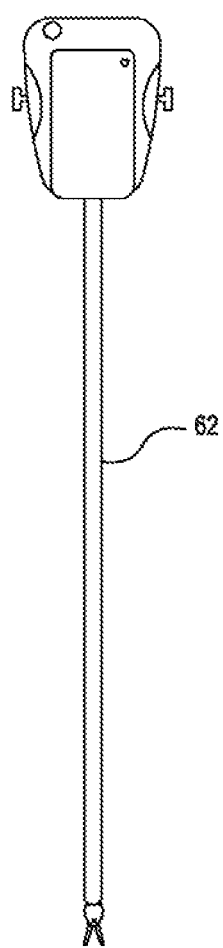
FIG. 5B is a front view of a telesurgically operated surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28. Each tool 26 is detachable from and carried by a respective surgical manipulator 31, which is located at the distal end of one or more of the robotic joints. The surgical manipulator 31 provides a moveable platform for moving the entirety of a tool 26 with respect to the Patient Side Cart 22, via movement of the robotic joints. The surgical manipulator 31 also provides power to operate the tool 26 using one or more mechanical and/or electrical interfaces. An example of such a carriage assembly is found at U.S. Patent Publication No. US 2013/0325034, which is incorporated by reference.

Figure 6:
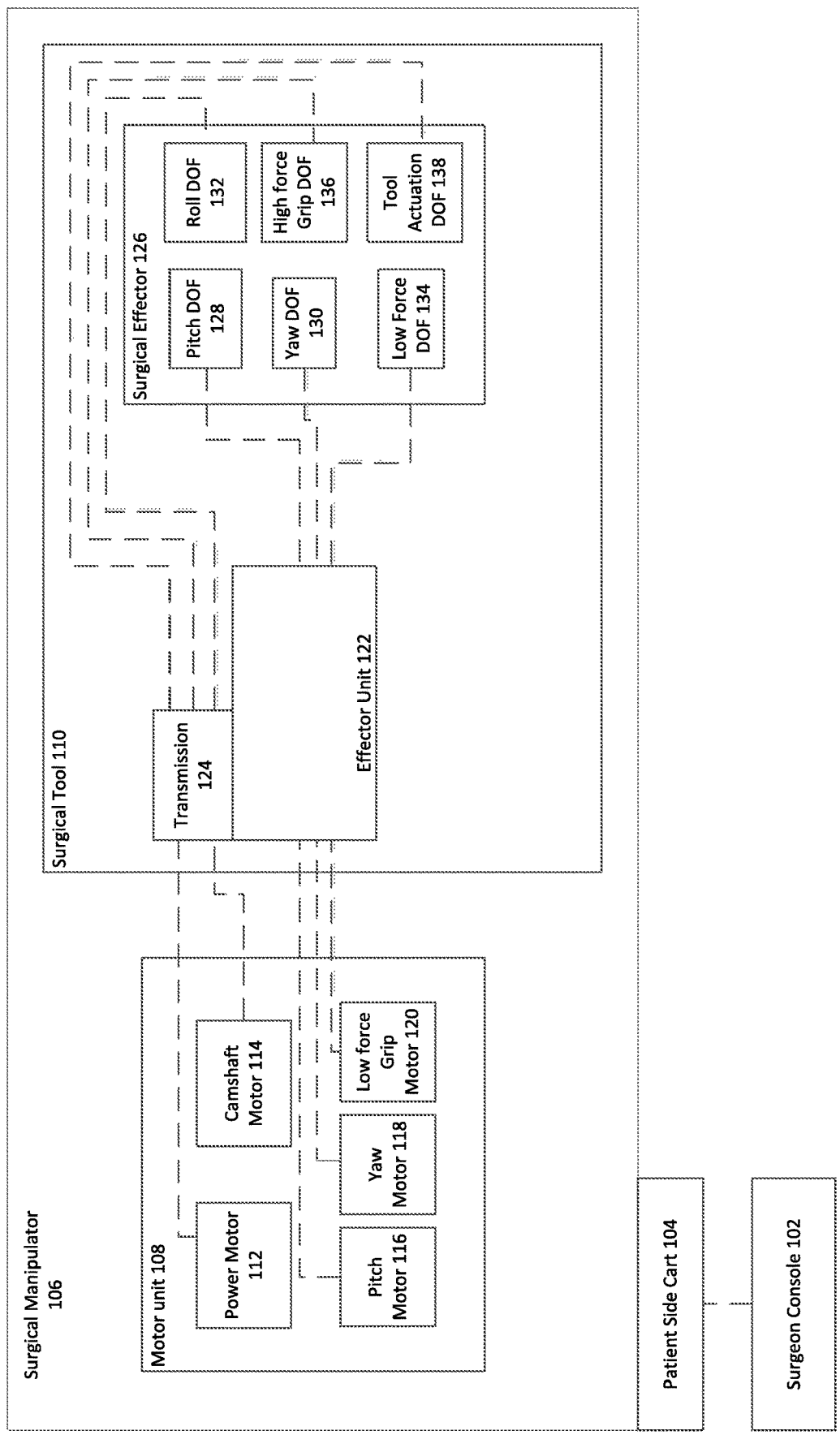
FIG. 6 is a simplified schematic diagram of a telesurgically controlled surgery system surgical system, in accordance with many embodiments.

FIG. 6 is a simplified schematic diagram of a telesurgically controlled surgery system surgical system 100. The surgical system 100 includes a surgeon console 102, which for example can be the Surgeon's Console 52. The surgeon console 102 drives a patient side cart 104, which for example can be the Patient Side Cart 22. The patient side cart 104 includes a surgical manipulator 106, which for example can be the surgical manipulator 31.

The surgical manipulator 106 includes a motor unit 108 and a surgical tool 110. The motor unit 108 is a carriage assembly that holds 5 motors. In some embodiments only 5 motors are used, while in other embodiments more or less than 5 motors can be used. Here, the motor unit 108 includes a plurality of motors, which can be assigned to different mechanisms. Here, the motor unit 108 includes a power motor 112, camshaft motor 114, pitch motor 116, yaw motor 118, and low-force grip motor 120, although these motors can be used for different purposes depending on the attached instrument. Generally, each motor is an electric motor that mechanically and electrically couples with corresponding inputs of the surgical tool 110. In some embodiments, the motor unit 108 may be located at a proximal end of the surgical tool 110 in a shared chassis with the surgical tool, as generally depicted by the proximal housing shown at FIG. 5B.

The tool 110 for example, can be the tool 26 described above. An example of a tool usable as tool 110 is at Int'l. Pub. No. WO 2011/060318, which is incorporated by reference. Here, the tool 110 is an elongated effector unit 122 that includes three discrete inputs that each mechanically couple with the pitch motor 116, yaw motor 118, and a low-force grip motor 120 by way of the surgical manipulator 106. The tool 110 also includes a transmission 124, which mechanically couples with the power motor 112 and the camshaft motor 114.

A surgical end effector 126 is located at the distal end of the effector unit 122. The surgical end effector 126 and effector unit 122 are connected by way of a moveable wrist. An example of such a wrist is shown at U.S. Patent Publication No. US 2011/0118709, which is incorporated by reference herein. In simplistic terms, the surgical end effector can be characterized by a plurality of discrete but interrelated mechanisms, with each mechanism providing a degree of freedom (DOF) for the surgical end effector 126. As used herein, a DOF is one or more interrelated mechanisms for affecting a corresponding movement. The DOFs endow the surgical end effector 126 with different modes of operation that can operate concurrently or discretely. For example, the wrist enables the surgical end effector 126 to pitch and yaw with respect to the surgical manipulator 106, and accordingly includes a pitch DOF 128 and a yaw DOF 130. The surgical end effector 126 also includes a roll DOF 132 rotating surgical end effector about an elongated axis.

The surgical end effector 126 may include a clamping and cutting mechanism, such as a surgical stapler. An example of such a clamping mechanism is shown at U.S. Patent Publication No. 2011-0118778 A1, which is incorporated by reference. The clamping mechanism can grip according to two modes, and accordingly includes two DOFs. A low-force DOF 132 (e.g., a cable actuated mechanism) operates to toggle the clamp with low force to gently manipulate tissue. The low-force DOF 132 is useful for staging the surgical end effector for a cutting or stapling operation. A high-force DOF 134 (e.g., a lead screw actuated mechanism) operates to further open the clamp or close the clamp onto tissue with relatively high force, for example, to tourniquet tissue in preparation for a cutting or stapling operation. Once clamped, the surgical end effector 126 employs a tool actuation DOF 138 to further affect the tissue, for example a stapling, cutting, and/or cauterizing device.

As shown, the pitch motor 116, yaw motor 118, and low force grip motor 120 drive the pitch DOF 128, yaw DOF 130, and low force grip DOF 139, respectively. Accordingly, each of the pitch DOF 128, yaw DOF 130, and low force grip DOF 139 is discretely paired with a motor, and can operate independently and concurrently with respect to other DOFs.

However, the high force DOF 126, roll DOF 132, and tool actuation DOF 138 share a single input with the power motor 112, via the transmission. Accordingly, only one of the high force DOF 126, roll DOF 132, and tool actuation DOF 138 can operate at one time, since coupling with the power motor 112 occurs discretely. The camshaft motor 114 is actuated to shift output of the power motor 112 between the high force DOF 126, roll DOF 132, and tool actuation DOF 138. Accordingly, the transmission 124 advantageously allows a greater amount of DOFs than an arrangement where each motor is dedicated to a single DOF.

II. Exemplary Transmission

Embodiments of invention relate to a system and method to control the 6 degrees of freedom (6 DOFs) of a stapler instrument with the 5 inputs allowable from a motor carriage. It takes one of the five inputs to use as a shifter, which then allows another input to be selectively engaged to three different stapler DOFs. The six DOFs of a stapler instrument can include wrist roll, wrist pitch, wrist yaw, low-force grip (toggle), high-force grip (clamp), and tool actuation (stapler fire). Wrist pitch, yaw, and low-force grip may be cable actuated, while roll, clamp, and fire are driven by independent sets of coaxial gears. In use, the transmission can include three main modes: roll, clamp/unclamp, and fire. Wrist rotation, pitch, yaw, and low-force grip are all under active servo control, and the high-force grip and fire DOFS are coupled to the roll axis.

In many embodiments, the driven input is selectively coupled to wrist roll, clamp, and/or fire. This is done through the use of idler gears that can be rotated in and out of engagement with the appropriate stapler DOF. Additionally, there is a method to lock each DOF to ground through the use of a lever arm. These lever arms are controlled by the shifting input, which can be a camshaft with the appropriate number and shapes of lobes. During a roll movement of the wrist, it is necessary for the clamp and fire input rings to rotate along with the roll gear. Because of this constraint, the gear ratios between the instrument input and the input rings and roll gear are all the same. That way, during the following state, all of the rings/gears are engaged, and therefore rotate together, so the fire and high-force grip drive shafts do not turn with respect to the wrist. The system can be configured so that all transitions move only one function at a time. This way all transitions are testable for safety. When transitioning out of following, the roll gear is locked. To avoid the necessity of the wrist needing to be positioned such that the roll gear is aligned with the teeth of the locking arm, there is a secondary friction lock on this DOF.

FIGS. 7A through 7H respectively show perspective and cross-sections of a transmission assembly 140. The transmission includes a gear train for each of the high force DOF 126, roll DOF 132, and tool actuation DOF 138.

A. First Gear Train

With attention to FIG. 7A, a first gear train 142 is located at the proximal end of the transmission assembly 140. The first gear train 142 drives the roll DOF 132 by axially rotating a main shaft 144. The main shaft 144 includes an axial passageway 146 for routing control cables to the surgical end effector 126. The main shaft 144 is directly rotated by driving external gear teeth 147 of a proximal gear 148.

B. Second Gear Train

A second gear train 150 is located directly adjacent to the first gear train 142, at a mid-portion of the transmission assembly 140. The second gear train 150 drives the high force grip DOF 126 by rotation of a middle shaft 152 with respect to the main shaft 144. The middle shaft 152 is held by the main shaft 144 and accordingly is rotated with the main shaft 144. Put another way, the axis of rotation of the middle shaft 152 can orbit about the axis of rotation of the main shaft 144.

The middle shaft 152 is directly connected to a middle internal gear 154, which in turn is driven by internal gear teeth (not shown in this view) of a middle gear 156. The middle gear 156 also includes external gear teeth 158 for directly driving the middle gear 156, ultimately by way of the power motor 112. The external gear teeth 158 of the middle gear 156 are configured identically to the external gear teeth 147 of the proximal gear 148. Accordingly, if driven synchronously, assuming identical input gears, there is no relative movement between the middle gear 156 and the proximal gear 148, and accordingly the middle shaft 152 is not driven with respect to main shaft 144.

An external portion of the main shaft 144 holds the middle gear 156 by way of two bearings. In a first disengaged state of the second gear train 150, the middle gear 156 (together with a distal gear 166 described below) can be configured to synchronously rotate with the main shaft 144 when both the middle gear 156 and are and proximal gear 148 are synchronously engaged with the power motor 112. In the first disengaged state, rotation of the middle gear 156 does not result in rotation of the middle internal gear 154, since the middle gear 156 is not allowed to roll with respect to the main shaft 144. Put another way, in the first disengaged state, the middle gear 156 clocks with the main shaft 144, and thus cannot move asynchronously with respect to the main shaft 144 to move the middle shaft 152. As discussed further below, the second gear train 150 includes a second disengaged state, in which the middle gear 156 is physically disengaged from the power motor 112 and physically locked, and thereby cannot rotate cannot drive the middle internal gear 154.

In an engaged state of the second gear train 150 (with the power motor 112), the proximal gear 148 and main shaft 144 are locked and therefore cannot rotate. Thus, the axis of rotation of the middle internal gear 154 cannot orbit about the axis of rotation of the main shaft 144. However, the middle internal gear 154 can spin about its own axis of rotation. Accordingly, in the engaged state, the middle gear 156 rotates with respect to the main shaft 144, and thereby drives the middle internal gear 154, ultimately by way of the power motor 112.

C. Third Gear Train

A third gear train 160 is located at a distal portion of the transmission assembly 140, and is largely configured in the same manner as the second gear train 150. The third gear train 160 drives the tool actuation DOF 138 by rotation of a distal shaft 162 with respect to the main shaft 144. The distal shaft 162 is held by the main shaft 144 and accordingly rotates with the main shaft 144. In the general manner as the second gear train 150, the axis of rotation of the distal shaft 162 can orbit about the axis of rotation of the main shaft 144.

The distal shaft 162 is directly connected to a distal internal gear 164, which in turn is driven by internal gear teeth (not shown in this view) of a distal gear 166. The distal gear 166 also includes external gear teeth 168 for directly driving the distal gear 166, ultimately by way of the power motor 112. The external teeth 168 of the distal gear 162 are configured in the same manner as the external gear teeth 147 of the proximal gear 148, as well as the external gear teeth 158 of the middle gear 156. Accordingly, when driven synchronously, there is no relative movement between the distal gear 166, middle gear 156 and proximal gear 148.

An external portion of the main shaft 144 holds the distal gear 166 by way of two bearings. In a first disengaged state of the third gear train 160, the distal gear 166 (together with the middle gear 156) can be configured to synchronously rotate with the main shaft 144 when both the distal gear 166 and are and proximal gear 148 are synchronously engaged with the power motor 112. In the first disengaged state, rotation of the distal gear 166 does not result in rotation of the distal internal gear 164, since the distal gear 166 is not allowed to roll with respect to the main shaft 144. Put another way, in the first disengaged state, the distal gear 166 clocks with the main shaft 144, and thus cannot move asynchronously with respect to the main shaft 144 to move the distal shaft 162. As discussed further below, the third gear train 160 includes a second disengaged state, in which the distal gear 166 is physically disengaged from the power motor 112 and physically locked, and thereby cannot rotate cannot drive the distal internal gear 164.

In an engaged state of the third gear train 160 (with the power motor 112), the proximal gear 148 and main shaft 144 are locked and therefore cannot rotate. In this manner, the axis of rotation of the distal internal gear 164 cannot orbit about the axis of rotation of the main shaft 144. However, the distal internal gear 164 can spin about its own axis of rotation. Accordingly, in the engaged state, the distal gear 166 rotates with respect to the main shaft 144, and thereby drives the distal internal gear 164, ultimately by way of the power motor 112.

D. Gear Train Construction

Figure 7B:
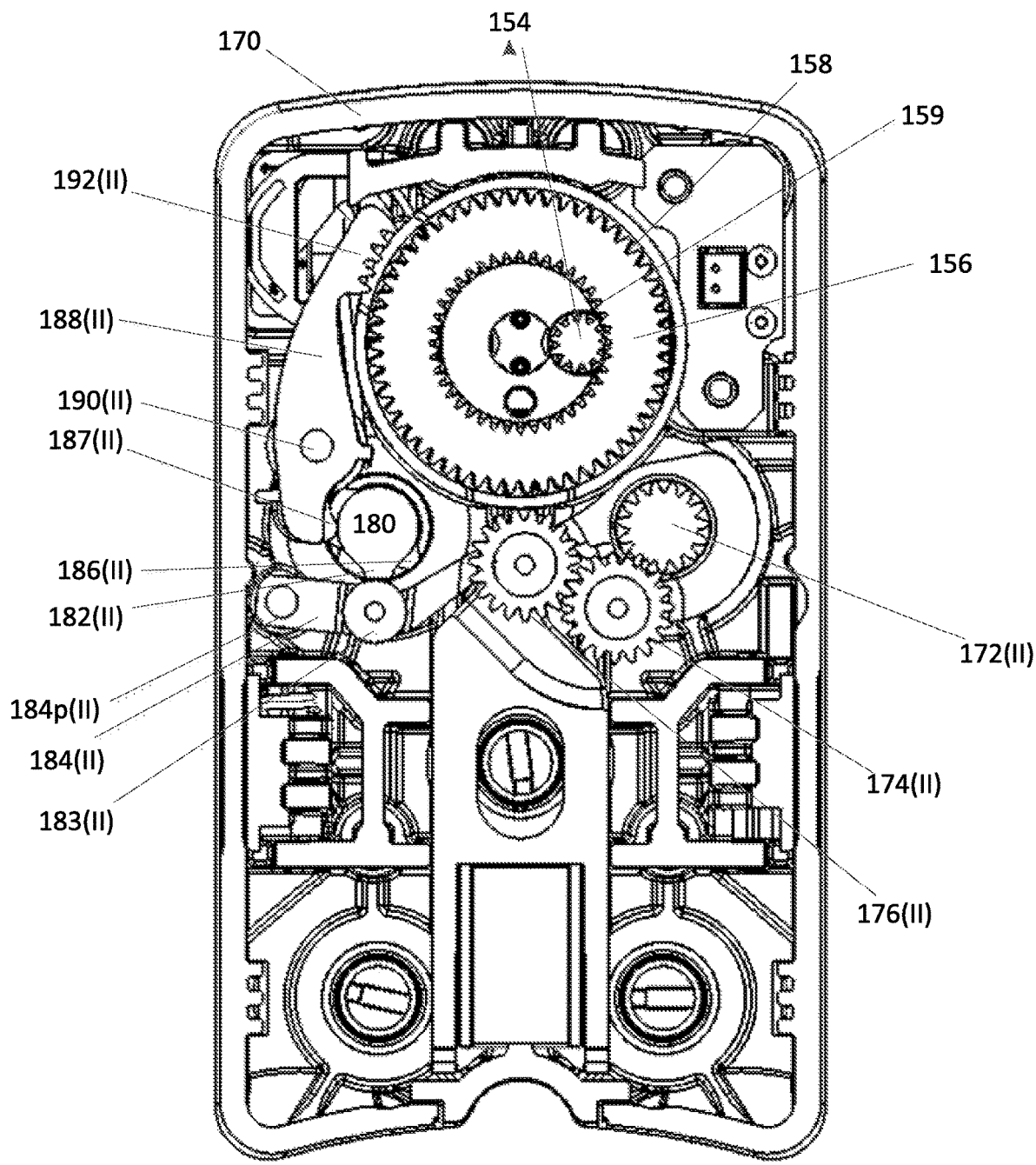
Figure 7D:
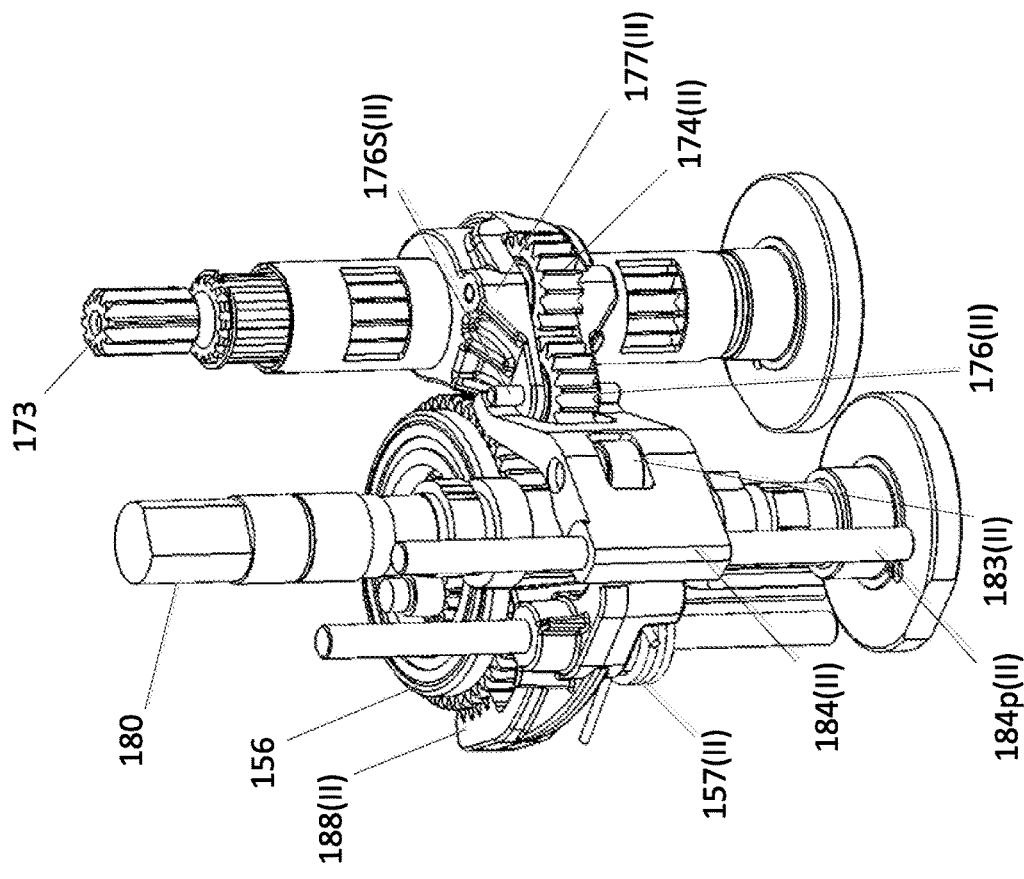
Figure 7C:
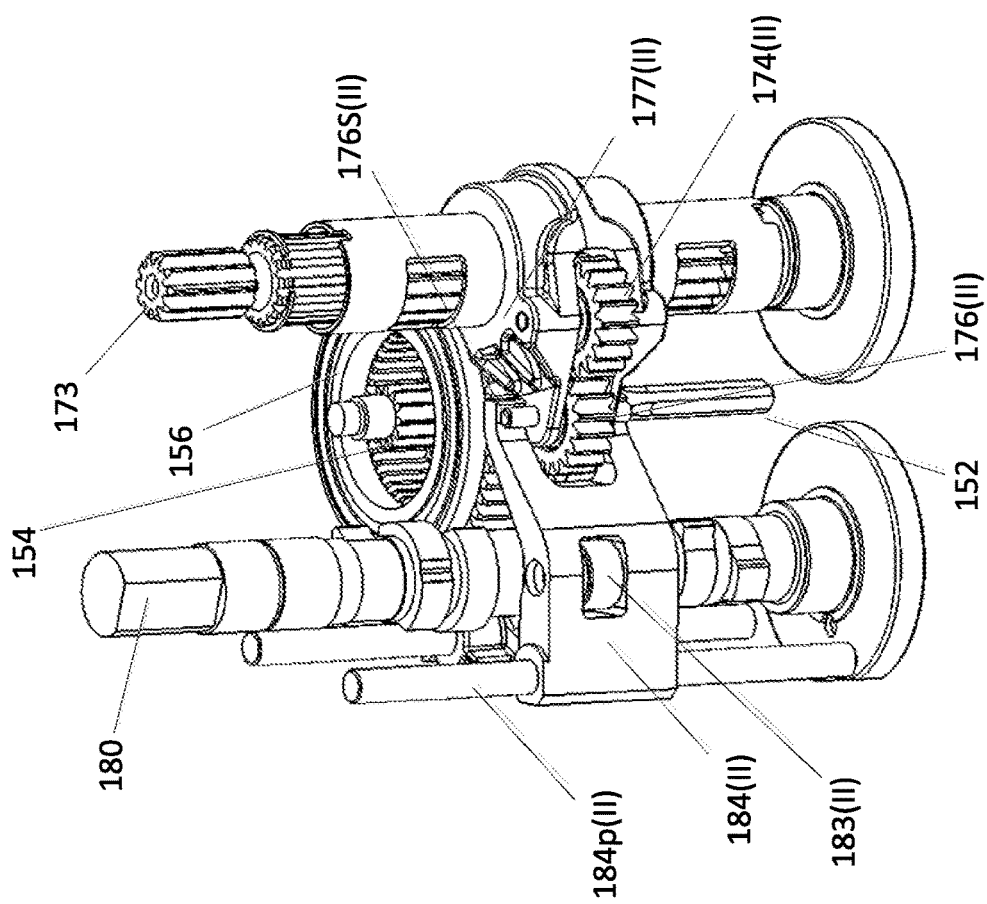
Figure 7E:
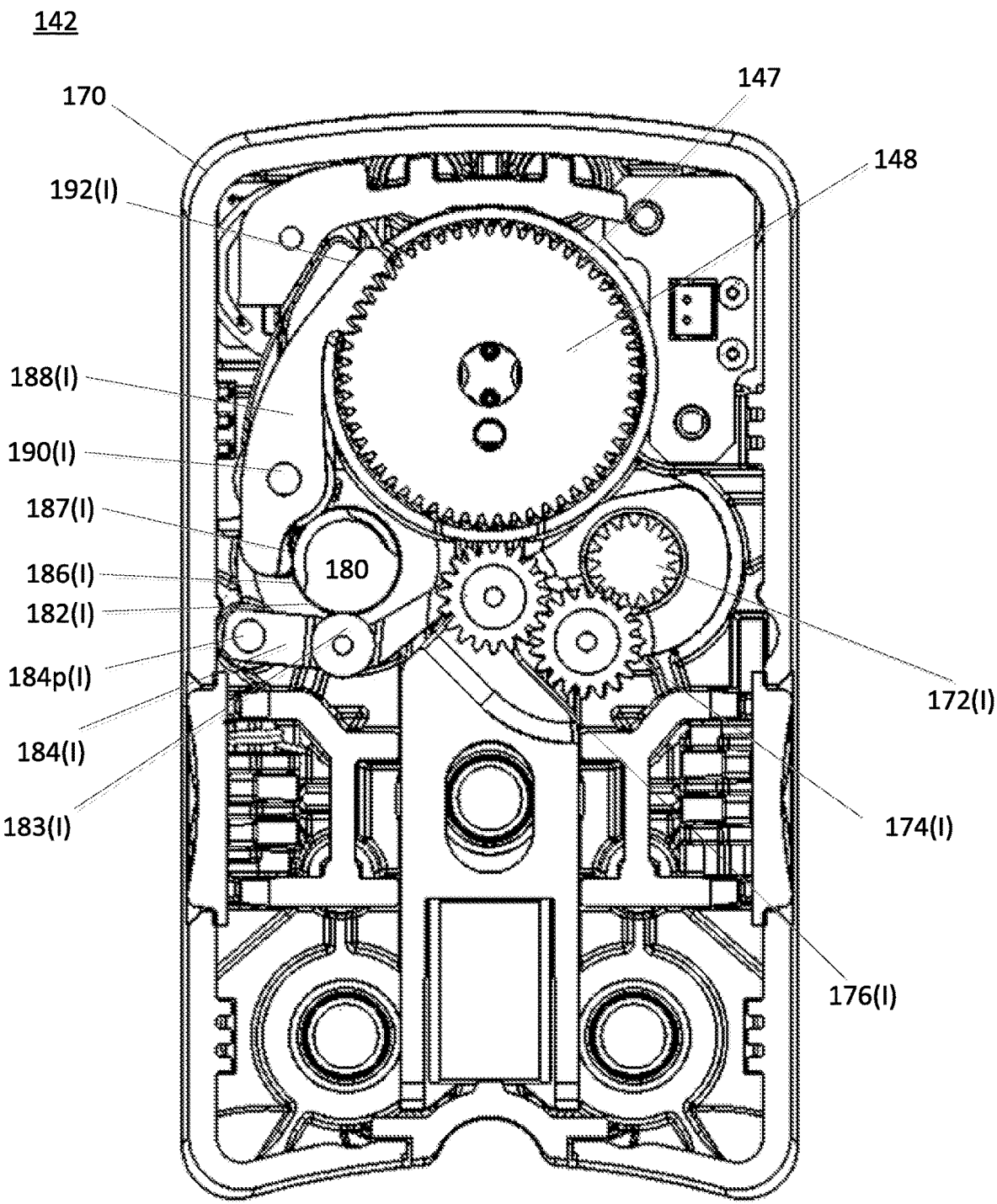
Figure 7F:
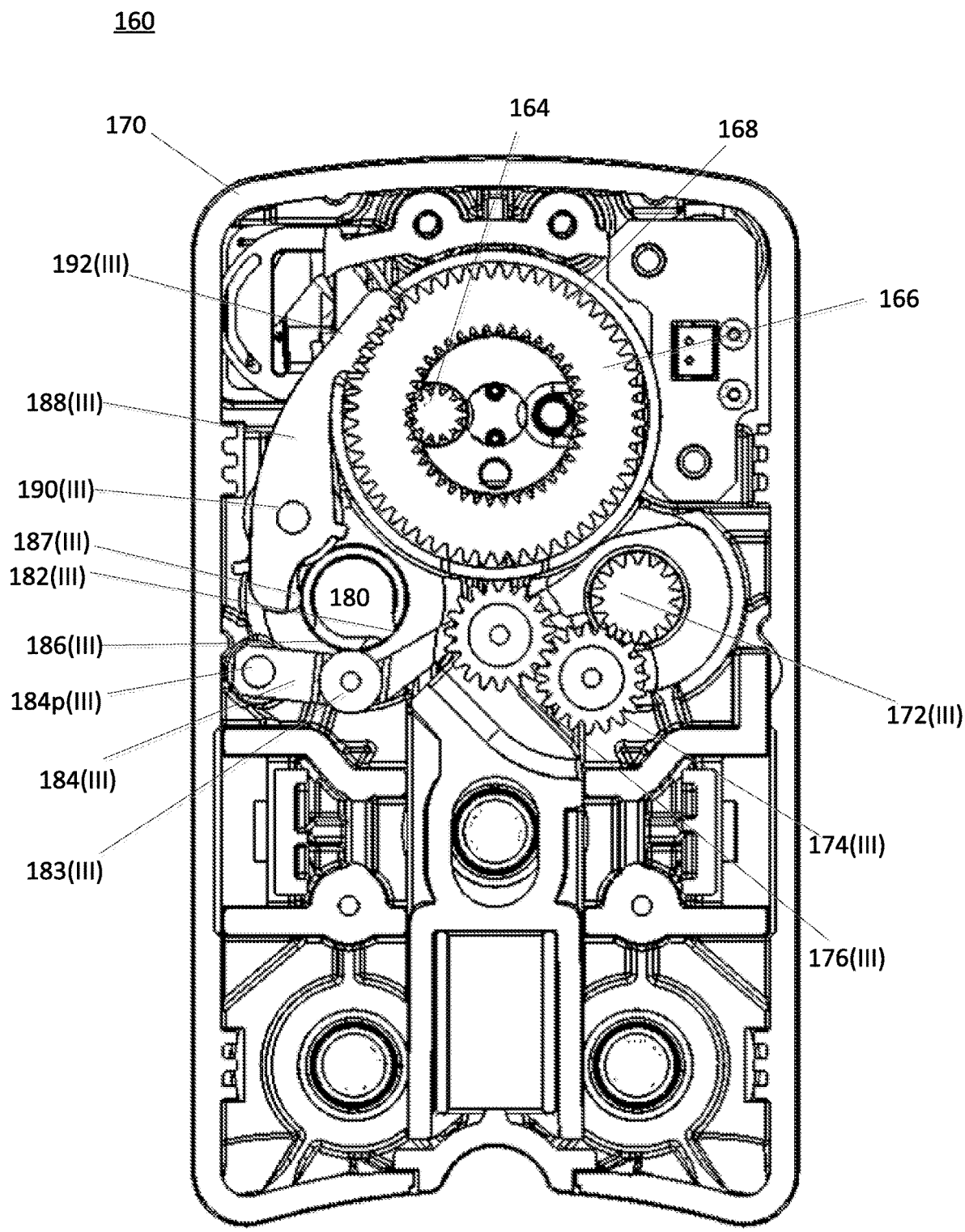

With attention to FIGS. 7B-D, a representative cross section and perspective views of the second gear train 150 is shown. FIGS. 7C and 7D have portions of the other gear trains removed to allow greater understanding of how a single gear train is configured. The first gear train 142 and third gear train 160 are configured in the same manner, accordingly, the following description applies in kind to FIGS. 7E and 7F, which respectively show representative cross-sections of those gear trains. To avoid unnecessary repetition, common numbering for similar parts between the gear trains is used. For example, locker arm 188(II) refers to the locker arm of the second gear train 150, and locker arm 188(III) refers to the locker arm of the third gear train. Each gear train operates essentially in the same manner, however, according to differing timing as determined by respective cam lobes of a shared camshaft as described below.

A greater housing 170 of the surgical tool 110 holds the transmission assembly 140. The power motor 112 drives a first input gear 172(II) via input shaft 173, as shown at FIGS. 7C and 7D, which is shared for each of the gear trains. The first input gear 172(II) is meshed with an idler gear 174(II), which in turn meshes with a second input gear 176(II) that can mesh with the middle gear 156. The idler gear 174(II) and second input gear 176(II) are on an arm 177(II), as shown at FIGS. 7C and 7D, that rotates about the first input gear 172(II). As shown, the second input gear 176(II) is positioned at the downward portion of the arc, and thereby is not meshed with the middle gear 156. The second input gear 176(II) can be moved to engage the second input gear 176(II) with the middle gear 156. A compression spring (not shown) is loaded between the second input gear shaft and housing 170 to bias the second input gear 176(II) towards the middle gear 156 such that middle gear 156 is engaged to power motor 112.

A camshaft 180 is disposed along the gear trains. The camshaft 180 generally includes at least two cam lobes per drive chain. The lobes rotate to engage and disengage a DOF mechanism with a gear train. The camshaft 180 is rotated by the camshaft motor 114 to selectively place the cam lobes into desired positions.

A first cam lobe 182(II) rotates to engage a bearing 183(II) of a rocker arm 184(II). The rocker arm 184(II) is moveable about a rocker pivot 184p(II). The rocker arm 184(II) extends to engage a gear shaft 176S(II), as shown at FIGS. 7C and 7D, of the second input gear 176(II). When a low portion of the first cam lobe 182(II) is engaged with the rocker arm 184(II), the second input gear 176(II) is engaged with the middle gear 156 as shown, due to the bias of the compression spring (not shown).

As shown, when a high portion of the first cam lobe 182(II) engages the bearing 183(II), the rocker arm 184(II) is moved downwardly about the rocker pivot 184p(II). Due to the engagement of the rocker arm 184(II) and the second input gear shaft 176S(II), this downward motion disengages the second input gear 176(II) from the middle gear 156(II). Accordingly, in this position of the first cam lobe 182(II), power applied to the first input gear is not translated to the middle gear 156.

A second cam lobe 186(II) rotates to engage a surface 187(II) of a locker arm 188(II), which pivots about locker arm pivot 190(II). The locker arm 188(II) includes a toothed portion 192(II) that can be moved to mesh the toothed portion 192(II) with the middle gear 156. A spring 157, as shown at FIG. 7D, is loaded between the locker arm 188(II) and housing 170 to bias the toothed portion 192(II) away from the middle gear 156.

As shown, when a low portion of the second cam lobe 186(II) engages the surface 187(II) of the locker arm 188(II), the toothed portion 192(II) is moved away from the middle gear 156. Accordingly, in this position the middle gear 156 is unlocked and allowed to rotate.

Figure 7G:
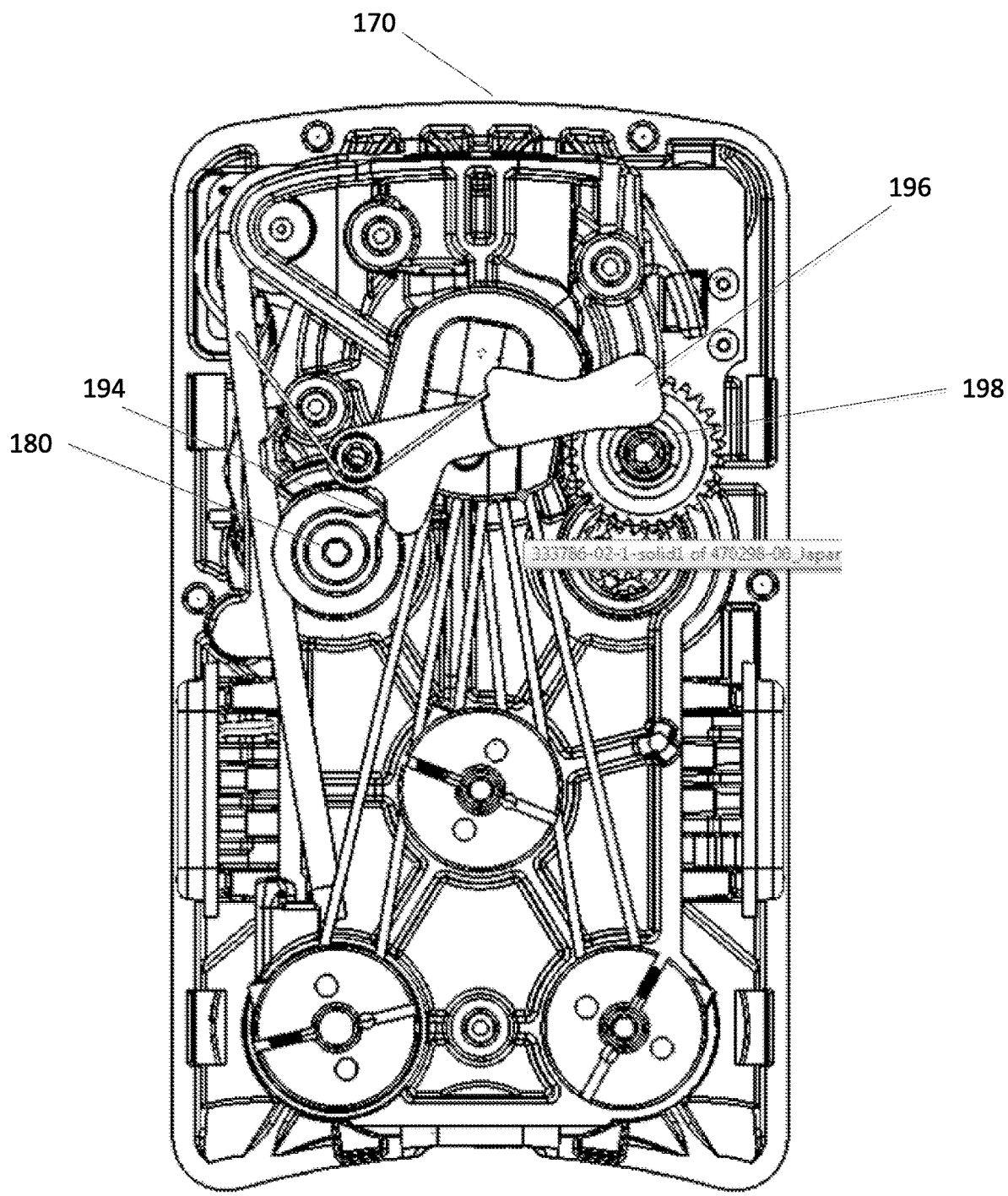

In the case of a system failure while the stapler is clamped on tissue, a manual unclamp feature is provided. In some embodiments, this can be accomplished by the user manually rotating the camshaft 180 to the high force grip DOF state, as described below. As shown at FIG. 7G, an interlock cam lobe 194 of camshaft 180 is moveable to a high state to move an interlock flag 196 that is rotatable and connected to a one-way clutch 198, which ultimately interfaces with the middle shaft 152. The end of the one-way clutch 198 is accessible by a handheld tool, such as a wrench, through a passage in the housing 170. The interlock flag 196 blocks the passage unless a high portion of the interlock cam lobe 194 is lifting the interlock flag 196 as shown. At the clamp state, the interlock flag 196 provides the user access to drive the middle shaft 152 via the one-way clutch 198 in a direction that only allows for the jaws to be unclamped.

Figure 7H:
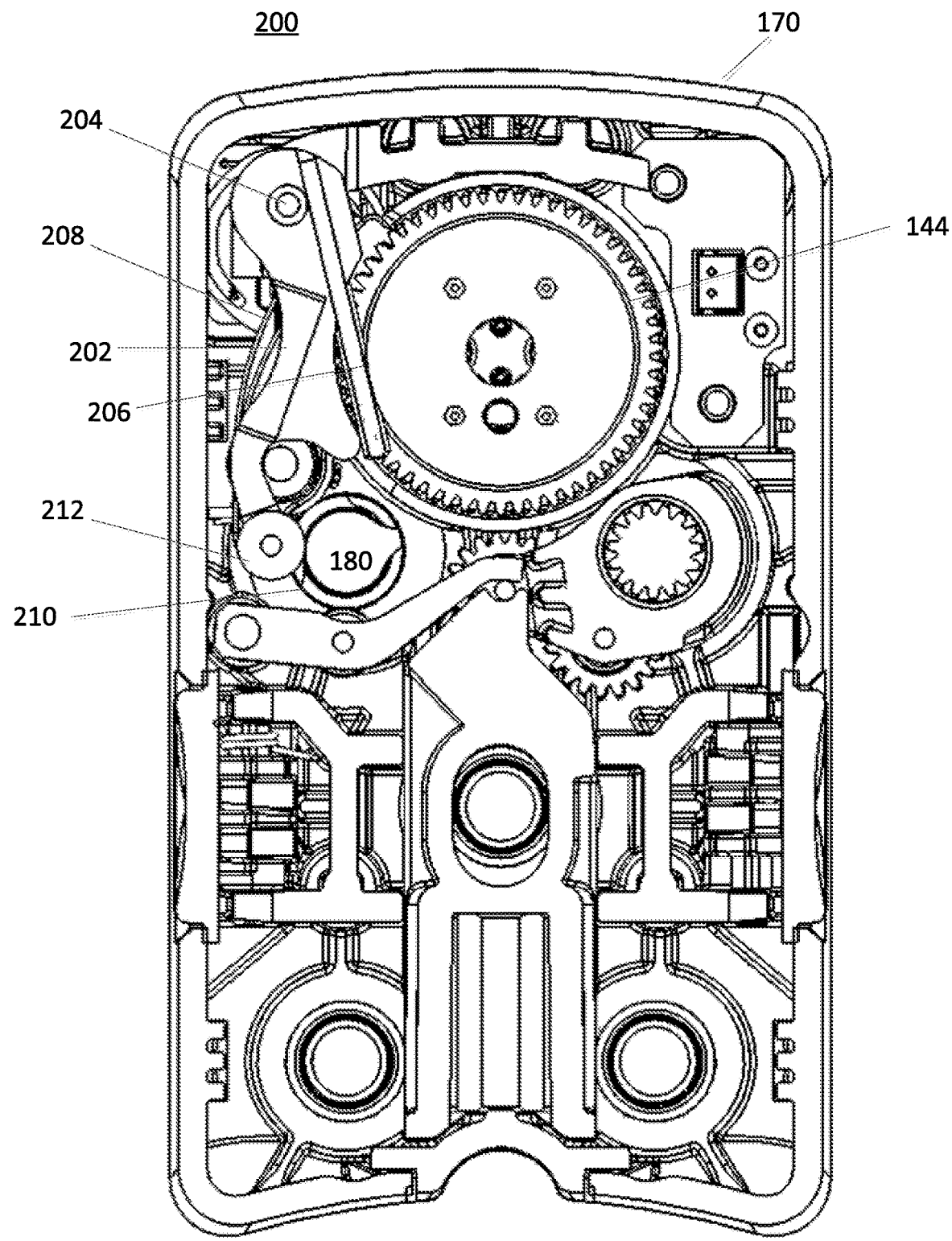

FIG. 7H depicts a friction lock mechanism 200, which acts as a secondary shaft braking system with respect to the locker arms 188(I-III). A friction lock arm 202 pivots about a pivot 204 and includes a brake surface 206. The friction lock arm 202 is biased by a spring 208 to place the brake surface 206 against a portion of shaft 144, as shown. In this position, the shaft 144 cannot roll. A friction lock cam lobe 210 of the camshaft 180 includes a high portion and a low portion. The shaft 144 will remain braked as long as the low portion of the friction lock cam lobe 210 is against a bearing 212 that positioned on the friction lock arm 202. The high portion can be rotated to lift a bearing 212 to position the friction lock arm away from the shaft 144. In that position, the shaft 144 is allowed to roll.

III. Transmission Shifting Method

When a high portion of the second cam lobe 186(I-III) engages the surface 187(I-III) of the locker arm 188(I-III), the toothed portion 192(I-III) is moved to engage the respective proximal gear 148, middle gear 156, or distal gear 166. This position locks the middle gear 156 with the locker arm 188, and accordingly, the middle gear 156 cannot move. One purpose of locking the middle gear 156 is to lock the last position of the high force grip DOF into a locked state. Generally, each gear train is locked in a similar manner, thus preventing unwanted movement.

Figure 8:
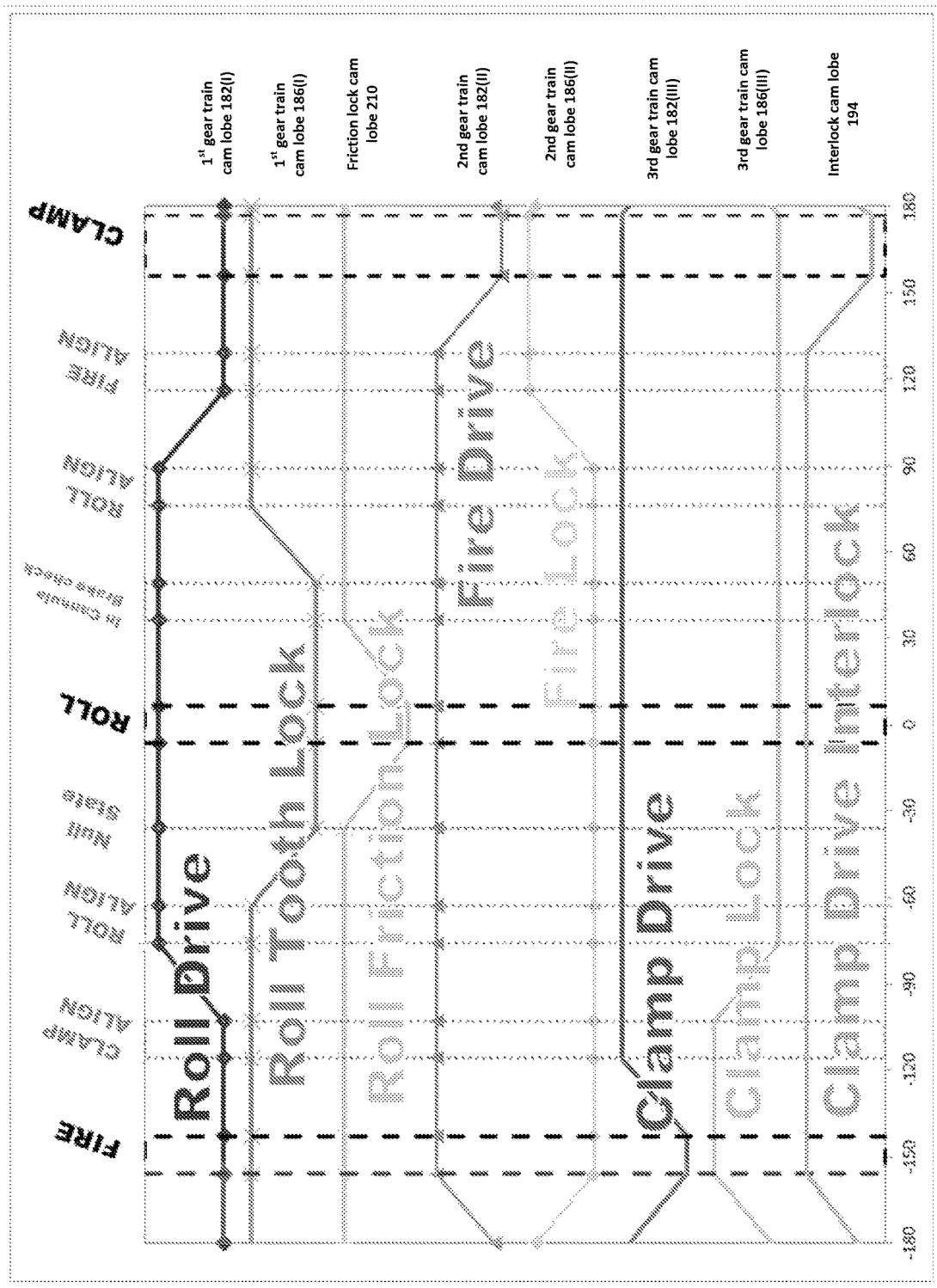
FIG. 8 shows a cam state chart for operation of the of a transmission assembly of a telesurgically operated surgery tool, in accordance with many embodiments.

The camshaft 180 is configured to operate the gear trains in harmony, which is achieved through camshaft timing. FIG. 8 shows a cam state chart for operation of the transmission 140. As discussed previously, the gear trains share a common camshaft, which for example is the camshaft 180 shown in FIGS. 7B-7D. The camshaft 180 provides each gear train with at least two lobes, e.g., the first cam lobe 182(I-III) and second cam lobe 186(I-III) operate with the first, second and third gear trains. However, some gear trains can include more lobes. For example, in some embodiments, the first gear train includes a third lobe to operate a friction lock. And as shown in FIG. 7G, additional lobes can be included as safely mechanisms to back drive DOFs in case of a system failure.

Generally, for each gear train, one cam lobe is operable to control power engagement and the other cam lobe is operable to lock the gear train. Accordingly, each gear train is operated by a power cam and a locker cam. In simplistic terms, each cam has a low state and a high state, with transitions ramps in between. The duration of each low and high state is based on the desired duration of operation of an object being lifted (e.g., the locker arm 188(I-III) and the rocker arm 184(I-III). For the purposes of this disclosure, a high state of the first cam lobe 182(I-III) means that the first cam lobe 182(I-III) is positioned such that an associated gear train is engaged with the power motor 112, while a low state of the first cam lobe 182(I-III) means disengagement. Similarly, a high state of the second cam lobe 186(I-III) means that the second cam lobe 186(I-III) is positioned such that an associated gear train is engaged with an associated locker arm 188(I-III), while a low state of the second cam lobe 186(I-III) means disengagement. It should also be understood that the outputs of the middle and distal gear trains not necessarily tied to the DOFs shown, and hence are interchangeable.

A. Cam State for First Transmission Mode

The cam state chart shows the low and high state for each cam over 360 degrees of rotation. At 0 degrees of rotation, the transmission 140 is configured to supply power for operation of the roll DOF 132 (ROLL). As shown, cam lobes 182(I-III) for each gear train is at a high state and cam lobes 186(I-III) for each gear train is at a low state. Accordingly, the first gear train 142 is unlocked and engaged with the power motor 112. In this manner, the locker arm 188(I) of the first gear train 142 is disengaged from the proximal gear 148 and the second input gear is engaged with the proximal gear 148. The second gear train 150 and the third gear train 160 are also unlocked, and the middle gear 156 and distal gear 166 remain in contact with the power motor. In addition, the friction cam lobe 210 for actuating the friction lock arm 202 is driven to a low state to allow the shaft 144 to turn.

As described above, during engagement of the roll DOF 132, the middle gear 156 and distal gear 166 are required to rotate in sync with the proximal gear 148, since the middle internal gear 154 and distal internal gear 164 are held within and rotate with the shaft 144. In this manner, relative movement is avoided between the middle gear 156/middle internal gear 154 and the distal gear 166/distal internal gear 164, thereby preventing operation of the middle shaft 152 and distal shaft 162. Accordingly, although the middle gear 156 and distal gear 166 remain engaged with the power motor 112 and thus are turned during a roll operation, the second gear train 150 and the third gear train 160 do not operate respective DOFs.

In addition, an "in cannula brake check" can be performed at approximately 40 degrees of rotation of the camshaft 180. In this mode, the friction lock arm 202 remains engaged with the shaft 144 but the locker arm 188(I) of the first gear train becomes disengaged, while the first gear train 142 remains engaged with the power motor 112. Because the locker arm 188(I) is disengaged, this allows the system to self-test the friction lock mechanism 200 by attempting to roll the braked shaft 144. If the shaft 144 is able to roll in this condition, it may be indicative that the friction lock mechanism 200 is malfunctioning.

B. Cam State for Second Transmission Mode

At approximately −150 degrees of rotation of the camshaft 180, the transmission is shifted to provide power to the tool actuation DOF 138 (FIRE). Here, the first cam lobe 182(I) of the first gear train 142 and the first cam lobe 182(III) of the third gear train 160 are at lows states and the first cam lobe 182(II) of the second gear train 150 is high. In this manner, the second input gears of the first gear train 142 and the third gear train 160 are respectively disengaged from the proximal gear 148 and the distal gear 166, while the second input gear of the second gear train 150 is engaged with the middle gear 156. Thus, only the middle gear 156 receives power from the power motor 112.

As shown, the second cam lobe 186(I) of the first gear train 142 and the second cam lobe 186(III) of the third gear train 160 are at high states, and the second cam lobe 186(II) of of the second gear train 150 is at a low state. In this manner, the locker arm 188(I) of the first gear train 142 and the locker arm 188(III) of the third gear train 160 are respectively engaged with the proximal gear 148 and the distal gear 166, while the locker arm 188(II) of the second gear train 150 is disengaged from the middle gear 156. Thus, only the middle gear 156 is free to turn.

C. Cam State for Third Transmission Mode

At approximately 170 degrees of rotation of the camshaft 180, the transmission is configured to provide power to the high force grip DOF 136 (CLAMP). Here, the first cam lobe 182(I) of the first gear train 142 and the first cam lobe 182(II) of the second gear train 150 are at low states and the first cam lobe 182(III) of the third gear train 160 is at a high state. In this manner, the second input gears of the first gear train 142 and the second gear train 150 are respectively disengaged from the proximal gear 148 and the middle gear 156, while the second input gear of the second gear train 150 is engaged with the middle gear 156. Thus, only the distal gear 166 receives power from the power motor 112.

In addition, the second cam lobe 186(I) of the first gear train 142 and the second cam lobe 186(II) of second gear train 150 are at high states and the second cam lobe 186(III) of the third gear train 160 is at a low state. In this manner, the locker arm 188(I) of the first gear train 142 and the locker arm 188(II) of the second gear train 150 are respectively engaged with the proximal gear 148 and the distal gear 156, while the locker arm 188(III) of the third gear train 160 is disengaged from the distal gear 166. Further, the interlock cam lobe 194 is driven to a high state, as described above with reference to FIG. 7G. This moves the interlock flag 196, and allows the user access to manually back drive the second gear train in case of a system failure.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A surgical tool comprising:
    an elongated shaft having a proximal end and distal end;
    a surgical end effector at the distal end of the shaft, the surgical end effector comprising a plurality of end effector components each associated with a unique mechanical degree of freedom, the plurality of end effector components comprising a first end effector component and a second end effector component; and
    a drive mechanism at the proximal end of the shaft, the drive mechanism comprising a first motor interface and a transmission, the transmission comprising a shift mechanism movable between a first state and a second state, in the first state the first motor interface being coupled via the transmission to drive the first end effector component without driving the second end effector component, in the second state the first motor interface being coupled via the transmission to drive the second end effector component without driving the first end effector component.

2. The surgical tool of claim 1, wherein:
    the drive mechanism includes a second motor interface coupled to shift the shift mechanism between the first state and the second state.

3. The surgical tool of claim 1, wherein:
    the plurality of end effector components comprises a third end effector component; and
    the shift mechanism is movable to a third state, in the first state and in the second state the first motor interface not driving the third end effector component, and in the third state the first motor interface being coupled via the transmission to drive the third end effector component without driving the first and second end effector components.

4. The surgical tool of claim 3, wherein:
    the drive mechanism includes a second motor interface coupled to shift the shift mechanism between the first state, the second state, and the third state.

5. The surgical tool of claim 1, wherein the shift mechanism includes a rotatable camshaft, a first position of the camshaft corresponding to the first state, and a second position of the camshaft corresponding to the second state.

6. The surgical tool of claim 5, wherein the drive mechanism further includes a second motor interface coupled to drive the camshaft.

7. The surgical tool of claim 1, wherein:
    the first end effector component is associated with a first end effector mechanical degree of freedom, and the second end effector component is associated with a second end effector mechanical degree of freedom; and
    the drive mechanism comprises a second motor interface coupled to drive a third end effector mechanical degree of freedom, a third motor interface coupled to drive a fourth end effector mechanical degree of freedom, and a fourth motor interface coupled to drive a fifth end effector mechanical degree of freedom; and
    the first, second, third, fourth, and fifth mechanical degrees of freedom of the end effector each being unique.

8. The surgical tool of claim 7, wherein:
    the plurality of end effector components comprises a third end effector component associated with a sixth end effector mechanical degree of freedom; and
    the first, second, third, fourth, fifth, and sixth mechanical degrees of freedom of the end effector each being unique.

9. The surgical tool of claim 8, further comprising:
the plurality of motor interfaces includes a fifth motor interface coupled to shift the shift mechanism between the first state and the second state.

10. The surgical tool of claim 9, wherein the surgical end effector comprises a gripping device having a surgical tool, wherein the surgical end effector includes a wrist, the wrist being able to pitch, yaw, and roll the gripping device with respect to the proximal end of the elongated shaft.

11. The surgical tool of claim 10, wherein:
the first end effector mechanical degree of freedom is for rolling the wrist;
the second end effector mechanical degree of freedom is for actuating the surgical tool;
the third end effector mechanical degree of freedom is for actuating the gripping device with high force relative to the sixth end effector mechanical degree of freedom;
the fourth end effector mechanical degree of freedom is for causing the wrist to yaw;
the fifth end effector mechanical degree of freedom is for causing the wrist to pitch; and
the sixth end effector mechanical degree of freedom is for actuating the gripping device with low force relative to the third end effector mechanical degree of freedom.

12. The surgical tool of claim 11, wherein the shift mechanism includes a rotatable camshaft comprising a plurality of camshaft lobes.

13. The surgical tool of claim 12, wherein the plurality of camshaft lobes comprises a pair of lobes for powering and locking each of the first, second, and third end effector mechanical degree of freedoms.

14. The surgical tool of claim 13, wherein the transmission comprises a first gear train for driving the first end effector mechanical degree of freedom, a second gear train for driving the second end effector mechanical degree of freedom, and a third gear train for driving the third end effector mechanical degree of freedom.

15. The surgical tool of claim 14,
wherein the first gear train comprises:
a first input gear;
a first output gear ultimately coupled with the first input gear;
a first rocker arm moveably engaged with the camshaft for engaging and disengaging the first input gear with the first output gear; and
a first locker arm moveably engaged with the camshaft for locking and unlocking the first output gear;
wherein the second gear train comprises:
a second input gear;
a second output gear ultimately coupled with the second input gear;
a second rocker arm moveably engaged with the camshaft for engaging and disengaging the second input gear with the second output gear; and
a second locker arm moveably engaged with the camshaft for locking and unlocking the second output gear; and
wherein the third gear train comprises:
a third input gear;
a third output gear ultimately coupled with the third input gear;
a third rocker arm moveably engaged with the camshaft for engaging and disengaging the third input gear with the third output gear; and
a third locker arm moveably engaged with the camshaft for locking and unlocking the third output gear.

16. The surgical tool of claim 15, wherein the first output gear is coupled to a main shaft extending along and rotatable about an axis, and wherein the second and third output gears are held within the main shaft and rotate with the main shaft about the axis.

17. The surgical tool of claim 16, wherein the second output gear is coupled to an first output shaft that extends within the main shaft, wherein the third output gear is coupled to an second output shaft that extends within the main shaft.

18. The surgical tool of claim 15, wherein the first, second, and third gear trains are arranged along a common axis that is parallel with the camshaft.

19. In a surgical device comprising a first motor interface, a transmission, and a surgical end effector comprising a first and a second component, a method comprising:
operating the transmission in a first state;
shifting the transmission from the first state to a second state;
operating the transmission in the second state; and
shifting the transmission from the second state to the first state;
the first state being one in which the transmission couples the first motor interface to the first component of the surgical end effector and decouples the first motor interface from the second component of the surgical end effector; and
the second state being one in which the transmission couples the first motor interface with the second component of the surgical end effector and decouples the first motor interface from the first component of the surgical end effector.

20. The method of claim 19, further comprising driving at least one of a plurality of non-shiftable effector outputs of the surgical end effector using a non-shiftable motor.

21. The method of claim 19, wherein shifting the transmission comprises driving a camshaft of the transmission using a second motor.

22. The method of claim 21, wherein driving the camshaft comprises rotating the camshaft to sequentially engage one of a plurality of gear trains.

23. The method of claim 22, wherein driving the camshaft causes a non-engaged gear train to become locked.

24. The method of claim 23, wherein driving the camshaft comprises rotating the camshaft to move a plurality of rocker arms that engage a plurality of gear trains of the transmission.

25. The method of claim 19, wherein a plurality of effector shiftable outputs includes a first shiftable output for actuating a roll end effector mechanical degree of freedom, and high force grip end effector mechanical degree of freedom, and a tool actuation end effector mechanical degree of freedom.

26. The method of claim 20, wherein the plurality of non-shiftable effector outputs drive a yaw end effector mechanical degree of freedom, pitch end effector mechanical degree of freedom, and a low force grip end effector mechanical degree of freedom.

* * * * *

UNITED STATES PATENT AND TRADEMARK OFFICE
CERTIFICATE OF CORRECTION

PATENT NO. : 10,610,313 B2
APPLICATION NO. : 15/129252
DATED : April 7, 2020
INVENTOR(S) : David W. Bailey et al.

It is certified that error appears in the above-identified patent and that said Letters Patent is hereby corrected as shown below:

In the Claims

Column 17, Lines 1-4, Please amend Claim 9 to read as follows:
-- The surgical tool of claim 8, further comprising a fifth motor interface coupled to shift the shift mechanism between the first state and the second state. --

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*